(12) United States Patent
Anderson et al.

(10) Patent No.: US 6,706,879 B2
(45) Date of Patent: Mar. 16, 2004

(54) FLUORESCENT DYE

(75) Inventors: Jack Anderson, Oceanside, CA (US); Jeffrey Carl Braman, Carlsbad, CA (US)

(73) Assignee: Stratagene, La Jolla, CA (US)

( * ) Notice: Subject to any disclaimer, the term of this patent is extended or adjusted under 35 U.S.C. 154(b) by 44 days.

(21) Appl. No.: 10/087,072

(22) Filed: Feb. 28, 2002

(65) Prior Publication Data

US 2003/0088109 A1 May 8, 2003

Related U.S. Application Data

(60) Provisional application No. 60/272,131, filed on Feb. 28, 2001.

(51) Int. Cl.[7] .......................... C09B 23/01; C07H 19/00; C07H 21/00; G01N 21/76
(52) U.S. Cl. .......................... 546/88; 548/120; 548/151; 548/218; 548/302.1; 548/433; 8/648; 435/6; 436/94; 436/172; 436/800
(58) Field of Search .............. 546/88; 548/120, 548/151, 218, 302.1, 433; 8/648; 435/6; 436/94, 172, 800

(56) References Cited

U.S. PATENT DOCUMENTS

| | | | |
|---|---|---|---|
| 5,268,486 A | 12/1993 | Waggoner et al. | 548/427 |
| 5,486,616 A | 1/1996 | Waggoner et al. | 548/217 |
| 5,556,959 A | 9/1996 | Brush et al. | 536/25.32 |
| 5,569,587 A | 10/1996 | Waggoner | 435/6 |
| 5,569,766 A | 10/1996 | Waggoner et al. | 548/150 |
| 5,571,388 A | 11/1996 | Patonay et al. | 204/461 |
| 5,627,027 A | 5/1997 | Waggoner | 435/6 |
| 5,639,874 A | 6/1997 | Middendorf et al. | 536/25.32 |
| 5,688,966 A | 11/1997 | Bobrow et al. | 548/455 |
| 5,767,287 A | 6/1998 | Bobrow et al. | 548/455 |
| 5,808,044 A | 9/1998 | Brush et al. | 536/25.32 |
| 5,853,992 A | 12/1998 | Glazer et al. | 435/6 |
| 5,986,086 A | 11/1999 | Brush et al. | 536/26.26 |
| 6,002,003 A | 12/1999 | Shen et al. | 544/232 |

FOREIGN PATENT DOCUMENTS

| | | | |
|---|---|---|---|
| EP | 0747488 | 12/1996 | C09B/23/04 |
| WO | WO97/13810 | 4/1997 | C09B/23/00 |
| WO | WO99/03849 | 1/1999 | C07D/277/64 |

OTHER PUBLICATIONS

Mikhailenko et al., Chemical Abstracts, 83:116913, 1975.*
Borisevich et al., Chemical Abstracts, 85:79659, 1976.*

* cited by examiner

*Primary Examiner*—Fiona T. Powers
(74) *Attorney, Agent, or Firm*—Kathleen M. Williams; Mark J. FitzGerald; Palmer & Dodge, LLP

(57) ABSTRACT

The invention relates to fluorescent dyes. More particularly, the invention relates to fluorescent cyanine dyes, and especially to water soluble fluorescent cyanine dyes that contain additional sites for attachment to biomolecules. The invention provides a group of novel, water soluble fluorescent cyanine dyes that have distinct fluorescence characteristics that permit their use in any assay or method suited to water soluble fluorescent dyes, and especially to assays requiring a plurality of distinguishable fluorescent markers. The invention further relates to nucleotides, nucleosides, polynucleotides and polypeptides labeled with novel fluorescent cyanine dyes according to the invention, and methods of using them.

49 Claims, 2 Drawing Sheets

Dyes Containing a Linear Fused Heterocycle.
Synthetic Scheme for the Synthesis of Dyes Containing
the Benzo[1,2-d:5,4-d']bisthiazole Moiety Dyes Containing an Angular Fused Heterocycle.
Synthetic Scheme for the Synthesis of Dyes Containing
the Benzo[1,2-d:3,4-d']bisthiazole Moiety

SEQUENCE LISTING

```
<160> NUMBER OF SEQ ID NOS: 1

<210> SEQ ID NO 1
<211> LENGTH: 73
<212> TYPE: DNA
<213> ORGANISM: Artificial Sequence
<220> FEATURE:
<223> OTHER INFORMATION: Amino oligonucleotide; 5' amino C-12
<220> FEATURE:
<221> NAME/KEY: misc_feature
<222> LOCATION: (1)..(1)
<223> OTHER INFORMATION: n is adenosine having a 5' amino C-12

<400> SEQUENCE: 1
naacccggga gctcgaattc cctataggta gtcgtattaa attcgtagtc atgtcataac      60
tgtttcctgt gtg                                                        73
```

FLUORESCENT DYE

This application claims the priority of U.S. Provisional Patent Application No. 60/272,131, filed Feb. 28, 2001.

BACKGROUND OF THE INVENTION

Fluorescent dyes are widely used for biological, biochemical or chemical applications in which a highly sensitive detection reagent is desirable. Molecules labeled with sensitive dye reagents enable the researcher to determine the presence, quantity or location of such molecules by monitoring their fluorescence. The quenching and energy transfer properties of fluorescent dyes also render the dyes useful for a variety of methods permitting investigators to monitor the in vivo and in vitro interactions between labeled molecules (e.g., protein:protein, protein:nucleic acid, nucleic acid::nucleic acid, and protein: or nucleic acid: interactions with drugs, drug candidates or other chemical entities). Fluorescent dyes are also useful for non-biological applications, such as photographic media.

In comparison to radiolabels frequently used for similar purposes, fluorescent dyes have the advantages of being safe to handle and dispose of and relatively stable. In addition, fluorescent dyes are detectable in real time, and differing fluorescence excitation and emission spectra can be exploited to permit differential detection of two, three or more different labeled species in a given mixture.

There is a wide variety of fluorescent dyes known and used in various fields. One class, the cyanine dyes, is very frequently used in biological and biochemical applications. Cyanine dyes are generally characterized by the presence of a pair of nitrogen-containing heterocycles ("terminal heterocycles") connected by a polymethine bridge over which bond resonance occurs. Most cyanine dyes exhibit high visible absorbance and reasonable resistance to photo-degradation. The general structure of cyanine dyes is given by the following formula:

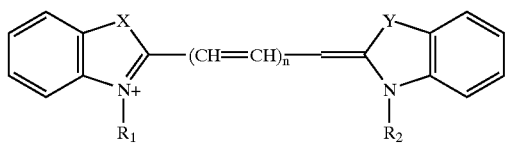

In the above formula, X and Y are typically heteroatoms (e.g., O, S, N) or disubstituted carbon atoms (e.g., C—($CH_3$)$_2$). Those dyes wherein n=0 are typically referred to as "cyanine" dyes. Where n=1 the dyes are termed "carbocyanine" dyes, while where n=2 the dyes are "dicarbocyanine" dyes and if n=3 the dyes are "tricarbocyanine" dyes, and so on. This class of dyes is generically referred to as "cyanine" dyes regardless of the specific number of methine groups between the ring systems.

The substituents $R_1$ and $R_2$ are typically saturated or unsaturated alkyl groups that are optionally further substituted by a wide variety of other functional groups. Other positions on the terminal heterocycles may be substituted with various organic functional groups, as well as additional fused or unfused rings that may themselves be additionally substituted.

There is a need in the art for additional fluorescent dyes. In particular, there is a need for dyes with fluorescence characteristics that permit distinct detection in multiple labeling assays, both in vitro and in vivo. Dye characteristics that can be altered to advantage include, for example, fluorescence excitation and emission spectra, fluorescence efficiency and quantum yield, fluorescence intensity, and characteristics such as solubility, chemical stability and compatibility with given assay conditions (e.g., in vitro, in vivo, aqueous, non-aqueous, etc.).

Fluorescence characteristics of the cyanine dyes can be altered, for example, by changing the aromatic nature of, or substituents on, the terminal heterocycles, or by changing the number of methine groups between the aromatic moieties. Generally, the longer the polymethine bridge, the higher the wavelengths of excitation and emission (i.e., longer polymethine bridges tend to shift excitation and emission spectra to the red, a so-called "red shift"). However, in general, the stability of the dye and the fluorescence efficiency decreases with increasing polymethine bridge length. It is desirable to alter fluorescence characteristics without dramatically increasing the size of the polymethine bridge.

SUMMARY OF THE INVENTION

The invention relates to novel fluorescent cyanine dyes and to molecules labeled with them. The dyes according to the invention are water soluble and can be used in any application normally requiring water soluble fluorescent dyes. The invention encompasses compositions comprising the novel fluorescent cyanine dyes disclosed herein, as well as nucleosides, nucleotides, polynucleotides, or other molecules or biomolecules labeled with such dyes.

In one aspect, fluorescent cyanine dyes according to the invention have a hetero cyclic structure integrated into the characteristic polymethine bridge between the terminal heterocycles that are characteristic of cyanine dyes. Dyes according to this aspect of the invention have longer emission wavelengths than dyes having similar terminal heterocycles but lacking the heterocycle integrated into the polymethine bridge.

In other aspects, the fluorescent cyanine dyes according to the invention have novel arrangements of functional groups for linkage to molecules of interest, novel combinations or arrangements of terminal heterocycles and/or structures providing structural rigidity. Each of the dyes according to these aspect of the invention has different fluorescence characteristics, making them useful for multiparameter assays and/or assays based on energy transfer.

The invention encompasses a fluorescent cyanine dye having the formula:

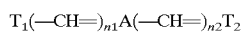

wherein: n≧1 and $n_1$ is the same as or different from $n_2$; A comprises the formula:

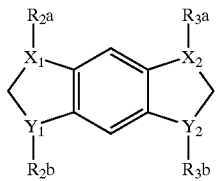

wherein: $X_1$ and $Y_1$ are selected from the group consisting of $C(CH_3)_2$, $CH=CH$, O, N, S, Se and Te and either $X_1$ or $Y_1$ is N; $X_2$ and $Y_2$ are selected from the group consisting of $C(CH_3)_2$, $CH=CH$, O, N, S, Se and Te and either $X_2$ or $Y_2$ is N; or A comprises the formula:

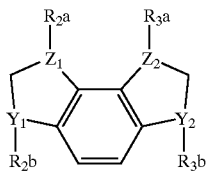

wherein: $Z_1$ and $Y_1$ are selected from the group consisting of $C(CH_3)_2$, $CH=CH$, O, N, S, Se and Te and either $Z_1$ or $Y_1$ is N; $Z_2$ and $Y_2$ are selected from the group consisting of $C(CH_3)_2$, $CH=CH$, O, N, S, Se and Te and either $Z_2$ or $Y_2$ is N; and wherein a and b are 0 or 1, and a+b=1; and where X, Y or Z is N, $R_2$ and $R_3$ are substituents on N and are the same or different and are selected from the group consisting of H, methyl, ethyl, $C(CH_3)_2$ and $(CH_2)_qV$, wherein q is an integer from 1 to 25 and V is a reactive group or H; and wherein T1 and T2 are the same or different and have the formula:

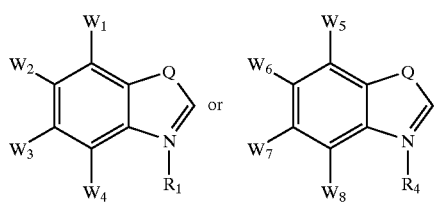

wherein: Q is selected from the group consisting of O, S, $CH_2$, $(CH=CH)$ and $C(CH_3)_2$; $R_1$ and $R_4$ are the same or different and are selected from the group consisting of H, methyl, ethyl and $(CH_2)_qV$, wherein q is an integer from 1 to 25 and V is a reactive group or H; each of $W_{1-8}$ is the same or different and may be H or a hydrophilic moiety; at least one occurrence of W is a hydrophilic moiety; and wherein at least one of $R_1$–$R_4$ has a reactive group.

In one embodiment, one or both of $Y_1$ and $Y_2$ are N. It is preferred that in the dye of this embodiment, one or both of $X_1$ and $X_2$ are S. It is also preferred in this embodiment that one or both of $X_1$ and $X_2$ are O. It is also preferred in this embodiment that one or both of $X_1$ and $X_2$ are $CH_2$. It is also preferred in this embodiment that one or both of $X_1$ and $X_2$ are $(CH=CH)$. It is also preferred in this embodiment that one or both of $Y_1$ and $Y_2$ are S.

In another embodiment, $Z_1$ and $Y_2$ are S.

In another embodiment, $Y_1$ and $Z_2$ are S.

In another embodiment, Q is $CH_2$.

In another embodiment, Q is $C(CH_3)_2$.

The invention further encompasses a composition comprising a dye as described above.

The invention further encompasses a fluorescent cyanine dye having the formula:

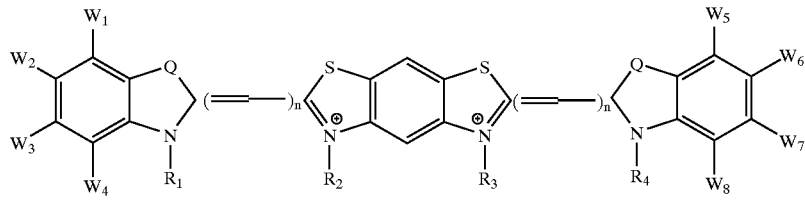

wherein: $n \geq 1$; Q is selected from the group consisting of O, S, $CH_2$, $(CH=CH)$ and $C(CH_3)_2$; $R_1$–$R_4$ are the same or different and are selected from the group consisting of H, methyl, ethyl and $(CH_2)_qV$, wherein q is an integer from 1 to 25 and V is a reactive group or H, and at least one of R1–R4 has a reactive group; each of $W_{1-8}$ is the same or different and may be H or a hydrophilic moiety; and at least one occurrence of W is a hydrophilic moiety. The invention also encompasses a composition comprising such a dye.

The invention further encompasses a fluorescent cyanine dye having the formula:

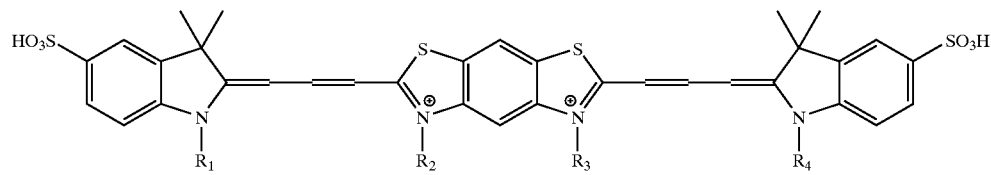

wherein $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group. The invention further encompasses a composition comprising such a dye.

The invention further encompasses a fluorescent cyanine dye having the formula:

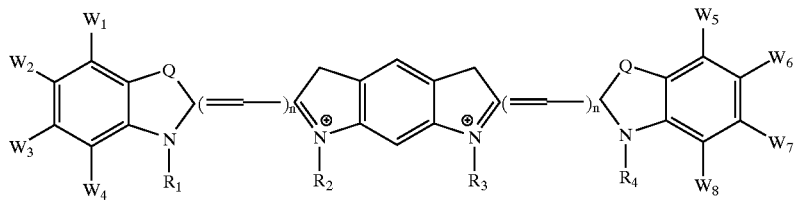

wherein: $n \geq 1$; Q is selected from the group consisting of O, S, $CH_2$, (CH=CH) and $C(CH_3)_2$; R1–R4 are the same or different and are selected from the group consisting of H, methyl, ethyl and $(CH_2)_qV$, wherein q is an integer from 1 to 25 and V is a reactive group or H, and at least one of R1–R4 has a reactive group; each of $W_{1-8}$ is the same or different and may be H or a hydrophilic moiety; and at least one occurrence of W is a hydrophilic moiety. The invention further encompasses a composition comprising such a dye.

The invention further encompasses a fluorescent cyanine dye having the formula:

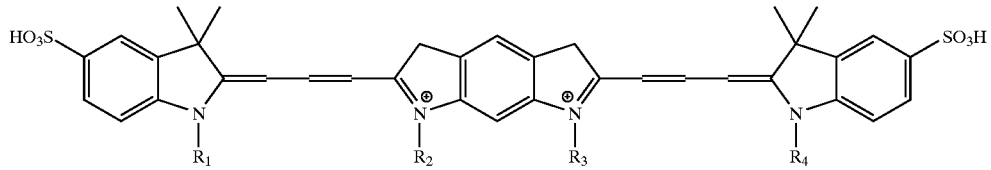

wherein $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group. The invention further encompasses a composition comprising such a dye.

The invention further encompasses a fluorescent cyanine dye having the formula:

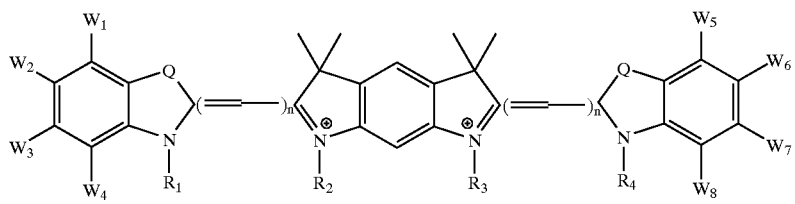

wherein: $n \geq 1$; Q is selected from the group consisting of O, S, $CH_2$, (CH=CH) and $C(CH_3)_2$; R1–R4 are the same or different and are selected from the group consisting of H, methyl, ethyl and $(CH_2)_qV$, wherein q is an integer from 1 to 25 and V is a reactive group or H, and at least one of R1–R4 has a reactive group; each of $W_{1-8}$ is the same or different and maybe H or a hydrophilic moiety; and at least one occurrence of W is a hydrophilic moiety. The invention further encompasses a composition comprising such a dye.

The invention further encompasses a fluorescent cyanine dye having the formula:

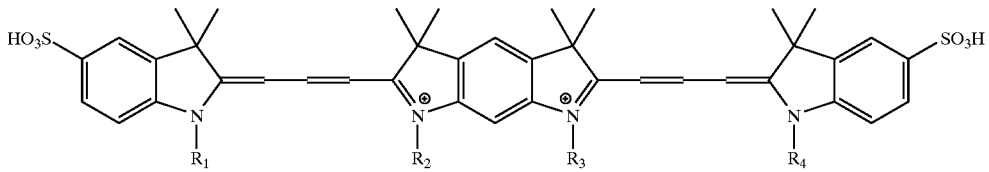

wherein $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group. The invention further encompasses a composition comprising such a dye.

The invention further encompasses a fluorescent cyanine dye having the formula:

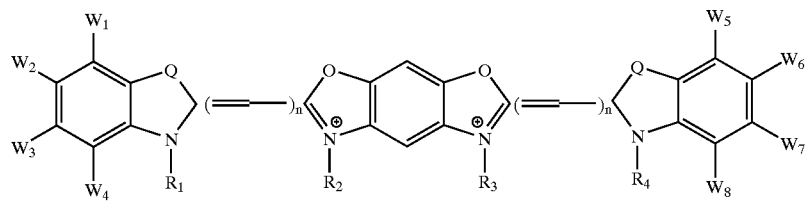

wherein: $n \geq 1$; Q is selected from the group consisting of O, S, $CH_2$, (CH=CH) and $C(CH_3)_2$; $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group; each of $W_{1-8}$ is the same or different and may be H or a hydrophilic moiety; and at least one occurrence of W is a hydrophilic moiety. The invention further encompasses a composition comprising such a dye.

The invention further encompasses a fluorescent cyanine dye having the formula:

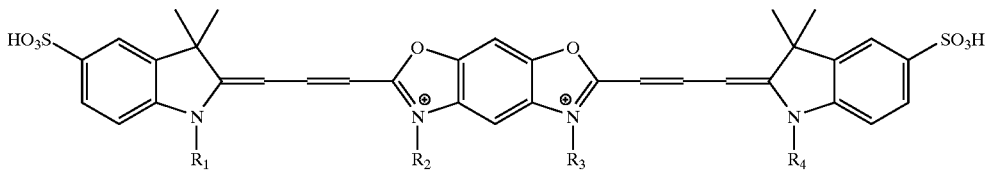

wherein $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group. The invention further encompasses a composition comprising such a dye.

The invention further encompasses a fluorescent cyanine dye having the formula:

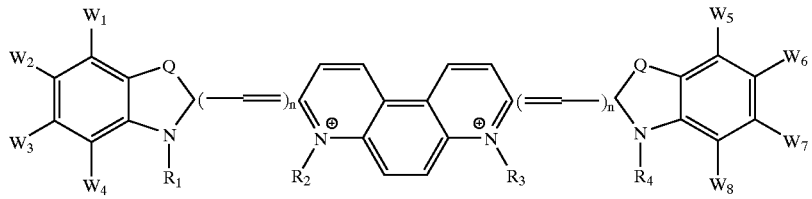

wherein: n≧1; Q is selected from the group consisting of O, S, CH$_2$, (CH=CH) and C(CH$_3$)$_2$; R$_1$–R$_4$ are the same or different and are selected from the group consisting of H, methyl, ethyl and (CH$_2$)$_q$V, wherein q is an integer from 1 to 25 and V is a reactive group or H, and at least one of R$_1$–R$_4$ has a reactive group; each of W$_{1-8}$ is the same or different and may be H or a hydrophilic moiety; and at least one occurrence of W is a hydrophilic moiety. The invention further encompasses a composition comprising such a dye.

The invention further encompasses a fluorescent cyanine dye having the formula:

methyl, ethyl and (CH$_2$)$_q$V, wherein q is an integer from 1 to 25 and V is a reactive group or H, and at least one of R$_1$–R$_4$ has a reactive group; each of W$_{1-8}$ is the same or different and may be H or a hydrophilic moiety; and at least one occurrence of W is a hydrophilic moiety. The invention further encompasses a composition comprising such a dye.

The invention further encompasses a fluorescent cyanine dye having the formula:

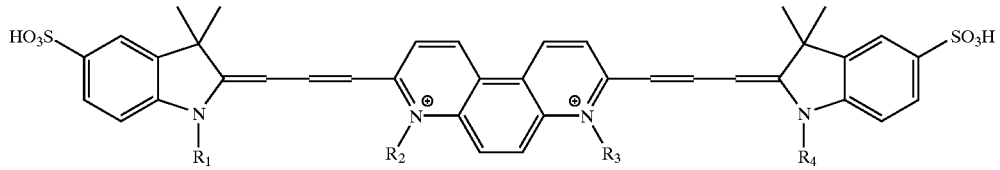

Wherein R$_1$–R$_4$ are the same or different and are selected from the group consisting of H, methyl, ethyl, C(CH$_3$)$_2$ and (CH$_2$)$_q$V, wherein q is an integer from 1 to 25 and V is a reactive group or H, and at least one of R$_1$–R$_4$ has a reactive group. The invention further encompasses a composition comprising such a dye.

The invention further encompasses a fluorescent cyanine dye having the formula:

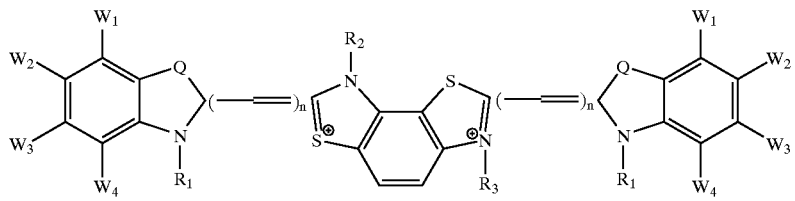

Wherein: n≧1; Q is selected from the group consisting of O, S, CH$_2$, (CH=CH) and C(CH$_3$)$_2$; R$_1$–R$_4$ are the same or different and are selected from the group consisting of H,

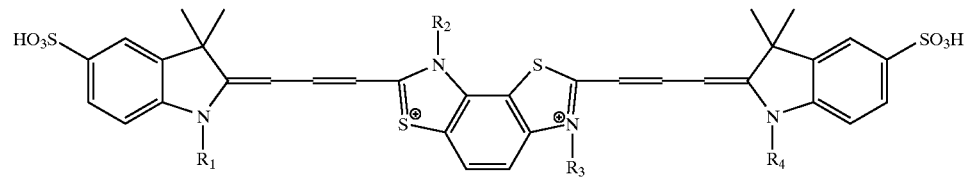

wherein $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group. The invention further encompasses a composition comprising such a dye.

The invention further encompasses a fluorescent cyanine dye having the formula:

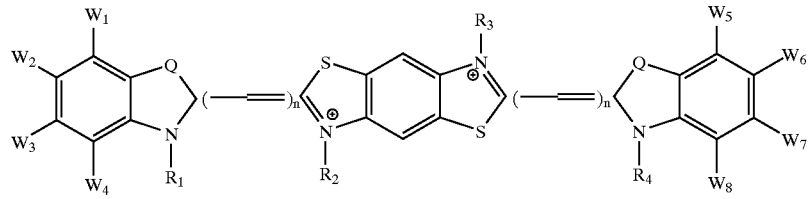

wherein: $n \geq 1$; Q is selected from the group consisting of O, S, $CH_2$, (CH=CH) and $C(CH_3)_2$; $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group; each of $W_{1-8}$ is the same or different and may be H or a hydrophilic moiety; and at least one occurrence of W is a hydrophilic moiety. The invention further encompasses a composition comprising such a dye.

The invention further encompasses a fluorescent cyanine dye having the formula:

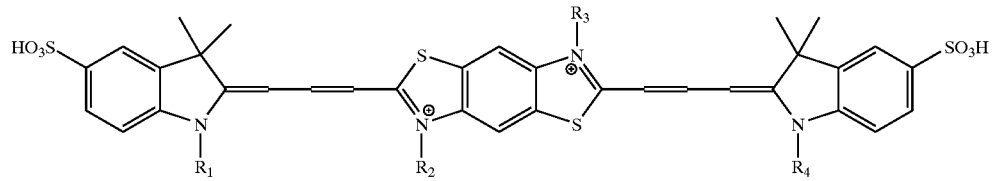

wherein $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group. The invention further encompasses a composition comprising such a dye.

The invention further encompasses a fluorescent cyanine dye as disclosed herein, wherein the dye further comprises a succinimide ester linked to a heterocyclic nitrogen.

The invention further encompasses a nucleoside or nucleotide labeled with a dye as disclosed herein.

The invention further encompasses a polynucleotide labeled with a dye as disclosed herein.

The invention further encompasses a polypeptide labeled with a flourescent cyanine dye as disclosed herein.

The invention further encompasses a method of labeling a nucleotide or nucleoside, the method comprising contacting a fluorescent cyanine dye of the invention with the nucleotide or nucleoside. In one embodiment, the dye comprises a reactive group and the nucleotide or nucleoside comprises a functional group complementary to the reactive group, wherein the contacting results in the covalent attachment of the dye to the nucleotide or nucleoside. In another embodiment, wherein the nucleotide or nucleoside comprises a reactive group and the dye comprises a functional group complementary to the reactive group, wherein the contacting results in the covalent attachment of the dye to the nucleotide or nucleoside.

The invention further encompasses a method of labeling a nucleic acid, the method comprising contacting a fluorescent cyanine dye of the invention with the nucleic acid. In one embodiment, the nucleic acid comprises a reactive group and the dye comprises a functional group complementary to the reactive group, wherein the contacting results in the covalent attachment of the dye to the nucleic acid. In another embodiment, the dye comprises a reactive group and the nucleic acid comprises a functional group complementary to the reactive group. In another embodiment, the nucleic acid comprises an allyl-amine-modified nucleotide, and the dye comprises an NHS group.

The invention further encompasses a method of labeling a polypeptide, the method comprising contacting a fluorescent cyanine dye of the invention with the polypeptide. In one embodiment, the method comprises contacting a polypeptide comprising a reactive group with a fluorescent cyanine dye of the invention, wherein the dye comprises a functional group complementary to the reactive group, and wherein the contacting results in the covalent attachment of the dye to the polypeptide.

The invention further encompasses a method of labeling a nucleic acid, the method comprising contacting the nucleic acid with a cis-platinum complex comprising a fluorescent cyanine dye of the invention.

The invention further encompasses a method of determining a nucleic acid sequence, the method comprising performing a nucleic acid sequencing reaction in the presence of a nucleotide labeled with a fluorescent cyanine dye of the invention. In one embodiment, the sequencing reaction is performed in the presence of a second nucleotide comprising a fluorescent dye that is spectrally distinct from the dye on the first nucleotide.

The invention further encompasses a method of determining a nucleic acid sequence, the method comprising determining a nucleic acid sequence on a nucleic acid comprising a fluorescent cyanine dye of the invention.

The invention further encompasses a method of detecting a polynucleotide, the method comprising detecting a polynucleotide comprising a nucleotide labeled with a fluorescent cyanine dye of the invention.

The invention further encompasses a method of detecting a polynucleotide, the method comprising detecting a polynucleotide comprising a fluorescent cyanine dye of the invention. In one embodiment, the method comprises hybridizing a nucleic acid probe comprising sequence complementary to the polynucleotide, wherein the nucleic acid probe comprises a fluorescent cyanine dye of the invention. In one embodiment, the detecting is performed on a nucleic acid microarray.

The invention further encompasses a method of detecting a polypeptide, the method comprising detecting a polypeptide comprising a fluorescent cyanine dye of the invention.

As used herein, the term "fluorescent" refers to the property of a molecule whereby, upon irradiation with light of a given wavelength or wavelengths, the molecule becomes excited and emits light of a longer wavelength or wavelengths. The term "fluorophore" as used herein refers to a fluorescent molecule. There are a number of parameters which together describe the fluorescence characteristics of a fluorophore. These include, for example, the maximum wavelengths of excitation and emission, the breadth of the peaks for excitation and emission, the difference between the excitation and emission maxima (the "Stokes shift"), fluorescence intensity, quantum yield, and extinction coefficient. For biological or biochemical applications, longer Stokes shifts are generally preferred to shorter ones.

Fluorescence intensity is determined as the product of the extinction coefficient and the fluorescence quantum yield. The fluorescence quantum yield is a measure of the relative efficiency or extent to which light energy absorbed is re-emitted as fluorescence. It is defined as the ratio of the number of fluorescence photons emitted, F to the number of photons absorbed, A, and molecules with larger quantum yields exhibit greater fluorescence intensity.

The molar extinction coefficient is a measure of a fluorophore's ability to absorb light. Commonly used fluorophores tend to have molar extinction coefficients (at their absorption maximum) between 5,000 and 200,000 $cm^{-1}M^{-1}$ (Haugland, R. P. (1996) *Molecular Probes Handbook for Fluorescent Probes and Research Chemicals*, 6th Edition). Because fluorescence intensity is the product of quantum yield and the extinction coefficient, higher extinction coefficients also correlate with greater fluorescence intensity.

As used herein, the term "water soluble" refers to a composition which dissolves in water. In order to be termed "water soluble" according to the invention, a fluorescent dye will form at least a 5 mM solution in water at room temperature (about 21° C.) and neutral pH. A water soluble fluorescent dye will preferably dissolve in water at neutral pH and room temperature to generate a solution that is at least 10 mM, 20 mM, 50 mM, 100 mM, 250 mM, 500 mM or more, up to and exceeding 1 M or more. The water solubility of a dye according to the invention may be increased by the addition of "hydrophilic moieties" at one or more sites on the molecule. "Hydrophilic moieties" are defined herein as polar or electrically charged groups that increase the water solubility of the dye molecule relative to the same dye molecule without the moiety. Examples of hydrophilic moieties include sulfonate, hydroxy, sulfate, sulfonate, carboxylate, phosphate, phosphonate, substituted amino or quaternary amino groups, or any of these groups attached to a lower alkyl group (lower alkyl groups have 10 or fewer carbon atoms).

In some embodiments, sulfonate groups are present on dyes according to the invention, increasing their water solubility. In other embodiments, however, the dyes lack sulfonate groups yet contain ionizable carboxylate ($COO^-$) moieties which confer water solubility on the free dye while also providing a convenient site for attachment to a biomolecule. The carboxylate group loses its charge upon attachment to a (water soluble) biomolecule (becoming an amide or peptide bond), however the final product retains water solubility as defined herein.

As used herein, the term "terminal heterocycle" refers to a nitrogen-substituted heterocycle located on either end of a polymethine bridge in a cyanine dye. In a dye according to the invention, at least one, and preferably both of the terminal heterocycles will comprise a quaternary nitrogen at the site of attachment to the polymethine bridge.

As used herein, the term "reactive group" refers to a chemical group which will react with a complementary functional group on a molecule of interest to form a covalent bond between the fluorescent dye to the molecule of interest. Reactive groups useful according to the invention include halomethyl ($-CH_2-X$), haloacetamide ($-NH-(C=O)-CH_2-X$), halomethylbenzamide ($-NH-(C=O)-C_6H_4-CH_2-X$) where X is Cl, Br or I. Reactive groups also include, but are not limited to an amine, a carboxyl, a thiol, maleimide, an azido, a (3,5-dichloro-2,4,6-triazin-1-yl) amino, an isocyanato, an isothiocyanato, an acyl halide, a succinimidyl ester, a sulfosuccinimidyl ester, a pentafluorophenyl, a 4-sulfotetrafluorophenyl, or a hydroxybenzotriazole group, among others.

As used herein, the term "polymethine bridge" refers to a chain of covalently bonded carbon atoms having alternating single and double bonds between them (e.g., $-CH=CH-CH=\ldots$; the methine group is $=CH-$), such that bond resonance between the single and double bonded state occurs over the length of the chain. A polymethine bridge joins nitrogens (at least one of which is, and preferably both of which are quaternary nitrogen(s)) comprised by two terminal heterocycles in a fluorescent dye according to the invention and will comprise at least two methine groups or at least four bonds which resonate between single and double bonded states. The polymethine bridge of a dye according to the invention can have substituted or unsubstituted cyclic structures comprising one or more rings integrated into it, as long as the bond resonance can still occur over the length of the whole bridge structure. The polymethine bridge structures of the dyes of the invention can confer structural stability on the dye, but their primary function is to allow electron resonance between the terminal heterocycle nitrogens joined by the polymethine bridge. This electron resonance permits absorbed excitation energy to be transmitted from one end of the fluorophore to the other during the process leading to fluorescent emission.

As used herein, the term "nucleotide" encompasses naturally occurring nucleotides, such as dATP, dCTP, dGTP, TTP, UTP, rATP, rCTP, rGTP, as well as synthetic or modified nucleotides such as ITP, and ddATP, ddCTP, ddGTP and ddTTP.

As used herein, the term "polynucleotide" refers to a double or single stranded chain of two or more phosphodiester-linked nucleotides. The term encompasses DNA, RNA, peptide nucleic acids (PNA) and heteroduplexes of these, as well as synthetic combination polynucleotides comprising one or more of DNA, RNA or a PNA chemically linked in one molecule.

As used herein, the term polypeptide refers to a molecule consisting of two or more amino acids joined by peptide bonds.

DESCRIPTION

Fluorescent Cyanine Dyes of the Invention

Figure 1:
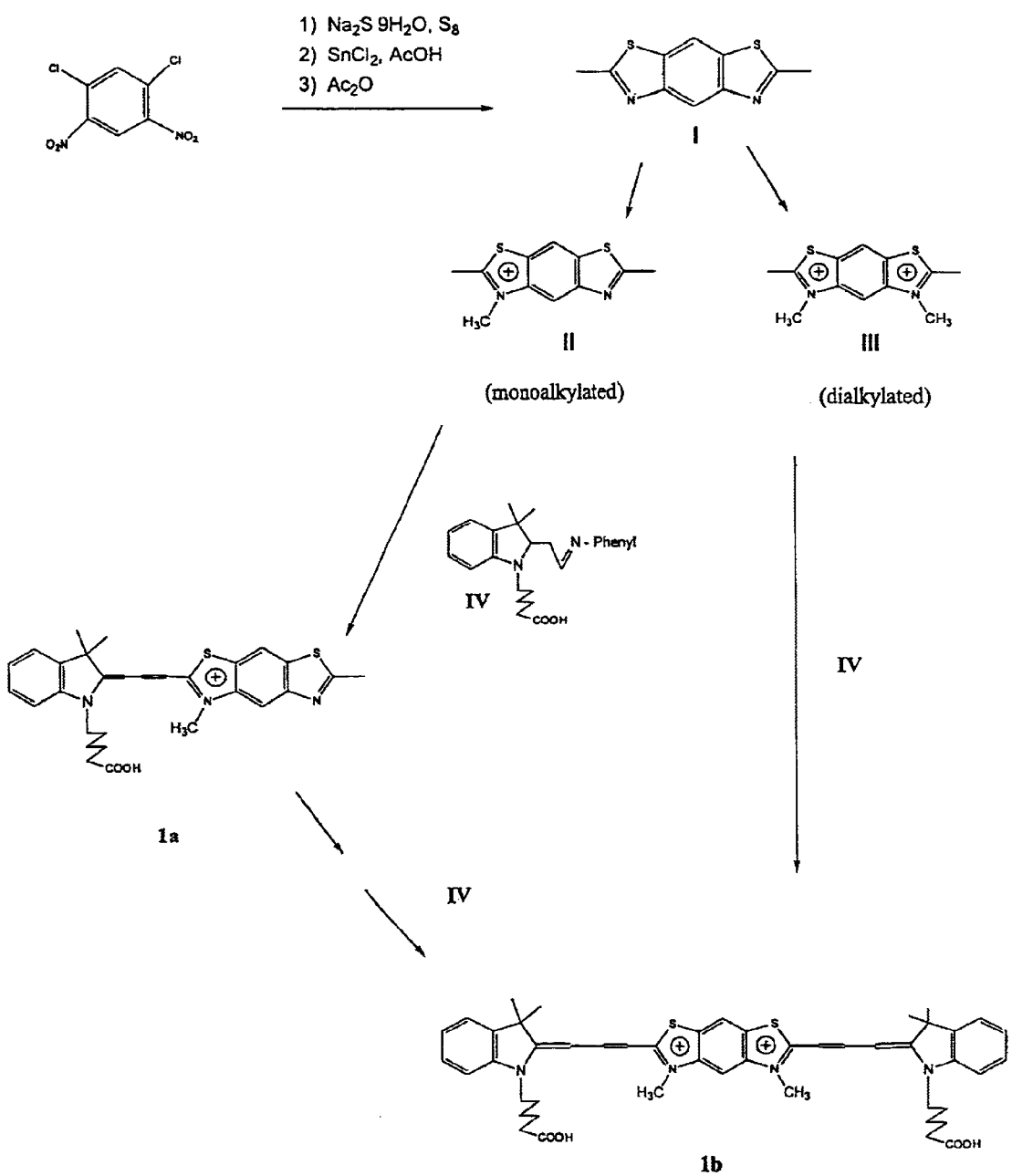
FIG. 1 shows a schematic diagram of steps involved in the synthesis of a dye comprising a linear fused heterocycle.

The invention provides novel water soluble cyanine dyes with fluorescence and chemical characteristics rendering them well suited for a variety of biochemical and non-biochemical uses. The dyes of the invention are particularly useful for labeling of carbohydrates, proteins, nucleic acids or nucleotides, and are therefore applicable to methods aimed at in vivo and in vitro detection, quantitation and localization of these molecules. The dyes are particularly well suited for monitoring molecular interactions among such molecules or between such molecules and other chemical moieties, such as drugs or drug candidates.

The cyanine dyes according to the invention may be symmetric or asymmetric. In a symmetric dye, the terminal heterocycles are identical, whereas the terminal heterocycles can have different structures in an asymmetric dye. Asymmetry can be useful in controlling the labeling process. For example, if a dye contains two or more functional groups (e.g., COOH), undesirable coupling events may occur in reactions aimed at labeling a biomolecule. The presence of two of the same reactive group can lead, for example, to the coupling of one dye molecule to two molecules of the labeling target. Therefore, it can be useful to design a dye in which the terminal indolenine moieties differ with respect to the functional groups attached to them. For example, a dye in which one indolenine contains a functional group (e.g., COOH) and the other contains a non-functional group (e.g., ethyl) will not suffer from the same biomolecule labeling difficulties possibly encountered where both indolenines have the same functional group. A dye with only one such functional group for attachment is termed a "monofunctional" dye.

In one embodiment, the cyanine dyes of the invention comprise a heterocyclic structure integrated into the polymethine bridge. This integrated heterocycle is referred to herein as the "central heterocycle". The designation as "central" is not meant to limit the location of the integrated heterocycle to the exact center of the polymethine bridge, but rather is meant to distinguish the integrated heterocycle from the terminal heterocycles located at either end of the polymethine bridge. Cyanine dyes having the integrated heterocyclic structures exhibit a shift in the emission spectrum to the red relative to similar dyes without central heterocycles.

The central heterocycle can additionally serve as a point of attachment of the dye to molecules of interest or to substituents that otherwise alter the chemical characteristics of the dye. The ability to attach the dye to a biomolecule (or other moiety) through the central heterocycle permits the addition of additional substituents on the terminal heterocycles that may provide further desired characteristics. For example, the solubility of the molecule or its ability to intercalate into a nucleic acid duplex may be modified by placing appropriate chemical substituents onto the molecule, and the presence of one or more alternate biomolecule attachment sites on the central heterocycle permits the placement of those substituents on the terminal heterocycles.

In one embodiment, the water soluble fluorescent dyes of the invention have the general formula:

$$T_1(=CH-)_{n_1}A(=CH-)_{n_2}T_2 \quad \text{(Formula 1)}$$

wherein $n\chi 1$ and $n_1$ is the same as or different from $n_2$, and A comprises at least three rings and has the formula of either Formula 2 or Formula 3:

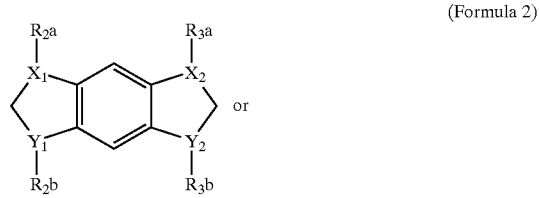

(Formula 2)

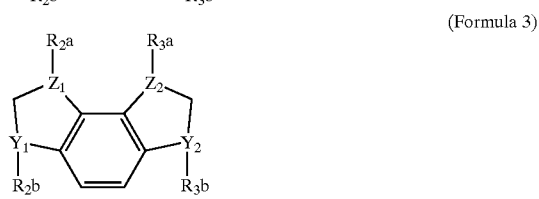

(Formula 3)

In the structure of Formula 2, $X_1$ and $Y_1$ are selected from the group consisting of $C(CH_3)_2$, CH=CH, O, N, S, Se and Te and either $X_1$ or $Y_1$ is N. Also in the structure of Formula 2, $X_2$ and $Y_2$ are selected from the group consisting of $C(CH_3)_2$, CH=CH, O, N, S, Se and Te and either $X_2$ or $Y_2$ is N.

In the structure of Formula 3, $Z_1$ and $Y_1$ are selected from the group consisting of $C(CH_3)_2$, CH=CH, O, N, S, Se and Te and either $Z_1$ or $Y_1$ is N. Also in the structure of Formula 3, $Z_2$ and $Y_2$ are selected from the group consisting of $C(CH_3)_2$, CH=CH, O, N, S, Se and Te and either $Z_2$ or $Y_2$ is N.

In Formulae 2 and 3, where X, Y or Z is (CH=CH), a six-membered ring is formed. Also in Formulae 2 and 3, a and b are 0 or 1, and a+b=1. Where X, Y or Z is N, $R_2$ and $R_3$ are substituents on N that are the same or different, and are selected from the group consisting of H, methyl, ethyl, $C(CH_3)_2$ and $(CH_2)_qV$, wherein q is an integer from 1 to 25 and V is a reactive group. Alternatively, the chain denoted as $(CH_2)_q$ in $(CH_2)_qV$ may be unsaturated at one or more sites, branched, and/or may contain one or more heteroatoms, substituents (including cyclic structures), or integrated ring structures.

The central ring of either of Formulae 2 or 3 may have additional substituents (e.g., sulfonate, phosphonate, halogen, branched or unbranched, substituted or unsubstituted alkyl or alkenyl, etc.).

The reactive group V is one which will react with a complementary functional group on a molecule of interest to covalently bind the fluorescent dye to the molecule of interest. Useful V groups include halomethyl (—CH$_2$—X), haloacetamide (—NH—(C=O)—CH$_2$—X), halomethylbenzamide (—NH—(C=O)—C$_6$H$_4$—CH$_2$—X) where X is Cl, Br or I. V groups also include an amine, a carboxyl, a thiol, maleimide, an azido, a (3,5-dichloro-2,4,6-triazin-1-yl) amino, an isocyanato, an isothiocyanato, an acyl halide, a succinimidyl ester, a sulfosuccinimidyl ester, a pentafluorophenyl ester, and carbodiimide, among others.

$T_1$ and $T_2$ in Formula 1 are the same or different and have the general formula:

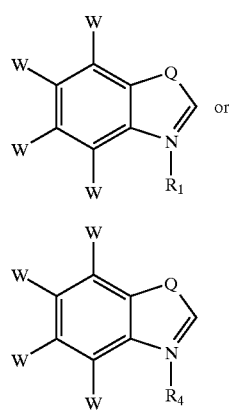

(Formula 4)

or (Formula 5)

In Formulae 4 and 5, Q is selected from the group consisting of O, S, CH$_2$, (CH=CH) and C(CH$_3$)$_2$. Where Q is (CH=CH), a six-membered ring is formed. Also, W is a hydrophilic moiety or H. Each occurrence of W is the same or different from the others, but at least one occurrence of W is a hydrophilic moiety on each of Formula 4 and Formula 5.

In Formulae 4 and 5, $R_1$ and R4 are selected from the group consisting of H, methyl, ethyl, and (CH$_2$)$_q$V, wherein q is an integer from 1 to 25 and V is a reactive group as described above. Alternatively, the chain denoted as (CH$_2$)$_q$ in (CH$_2$)$_q$V may be unsaturated at one or more sites, branched, and/or may contain one or more heteroatoms, substituents (including cyclic structures), or integrated ring structures.

A fluorescent dye molecule according to the invention comprises at least one reactive group linked to a heterocyclic nitrogen. For example, in a molecule according to Formula 1, which comprises either of Formulae 2 or 3 and further comprises Formula 4 and/or 5, at least one of $R_1$–$R_4$ will have a reactive group, preferably a terminal reactive group.

In a preferred embodiment, the water soluble fluorescent cyanine dye has the structure of any one of Formulae 6–19 below, wherein W, V, n and Q are as described above:

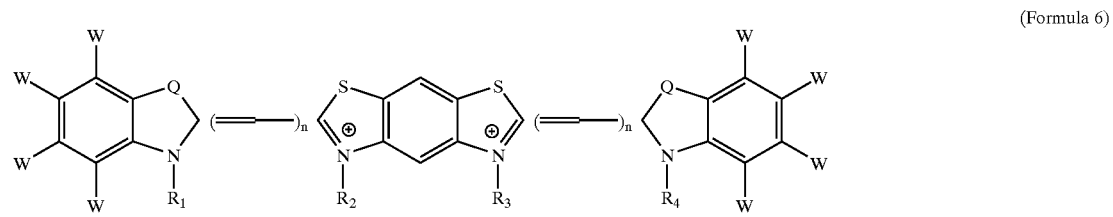

(Formula 6)

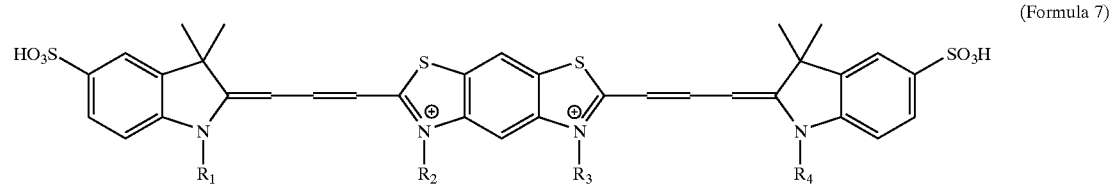

(Formula 7)

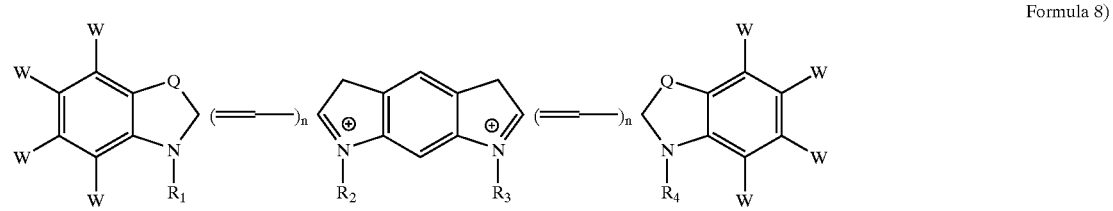

(Formula 8)

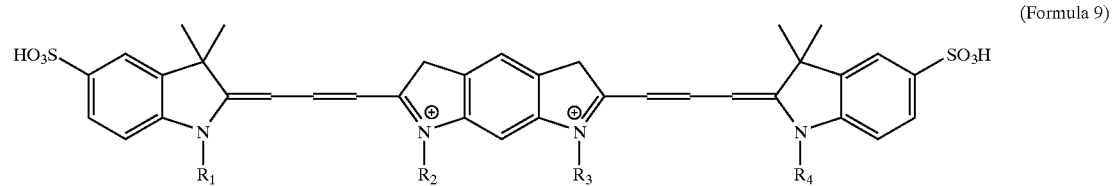

(Formula 9)

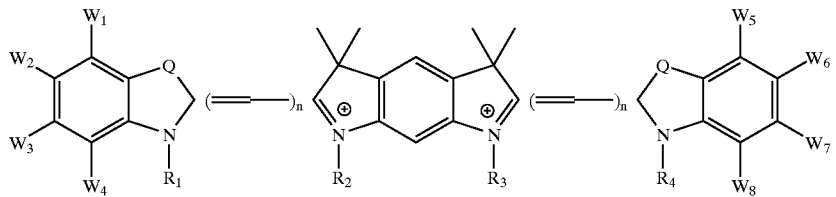
(Formula 10)
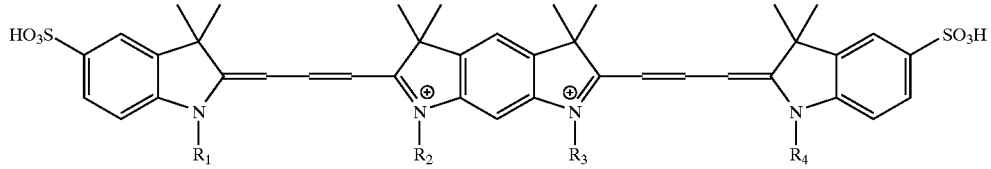
(Formula 11)
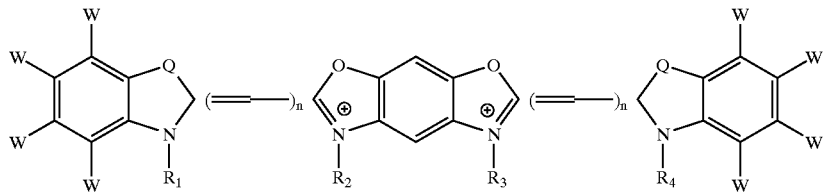
(Formula 12)
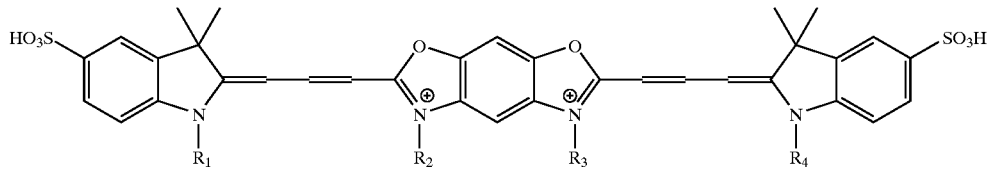
(Formula 13)
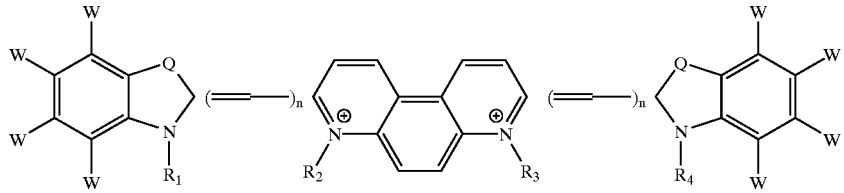
(Formula 14)
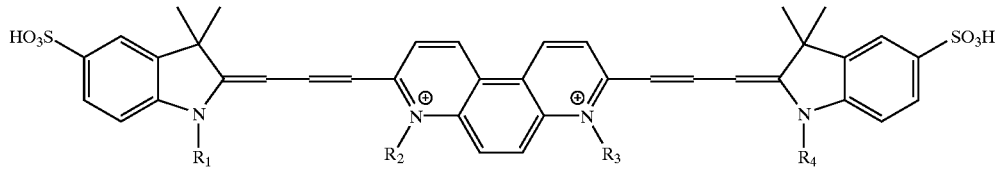
(Formula 15)
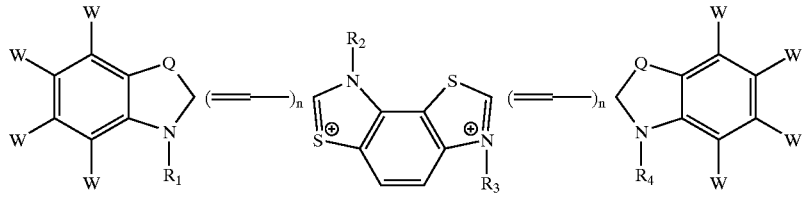
(Formula 16)
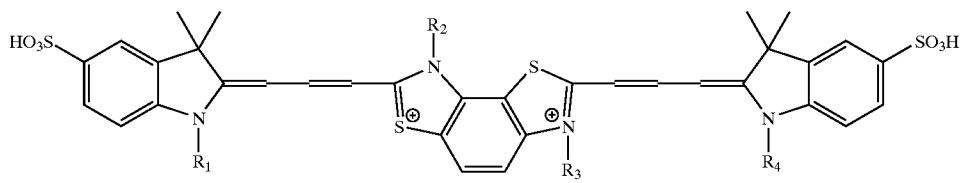
(Formula 17)

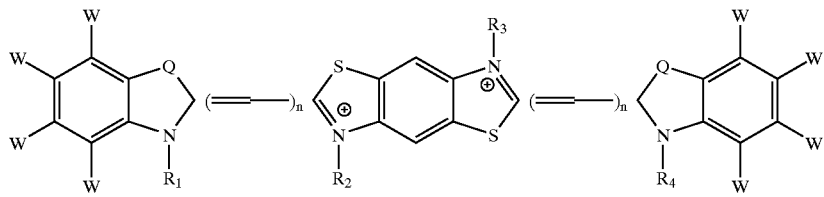
(Formula 18)

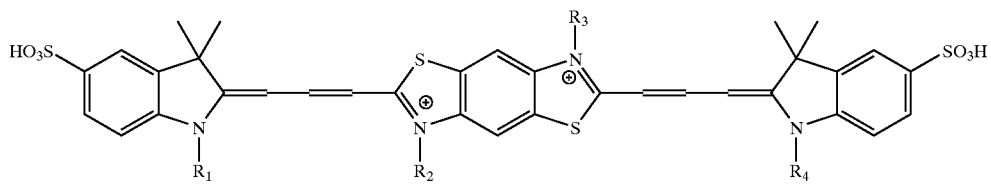
(Formula 19)

The fluorescence characteristics of molecules according to Formula 1 are influenced by the general structure of the molecule (e.g., the identity and makeup of the basic ring structure of the terminal heterocycles), as well as by the substituents on those structures. For example, it has been found that the presence of dimethyl substituents on the atoms identified as $X_1$ and $X_2$ in Formula 2 renders a molecule according to Formula 11 much more intensely fluorescent than a molecule according to Formula 9, which is identical except for the dimethyl substituents on the central heterocycle. Fluorescence characteristics that can be influenced by the presence or identity of substituents on the terminal or central heterocycles include, for example, the extinction coefficient or intensity of emission, quantum yield or efficiency of emission, and resistance or susceptibility to photobleaching.

Any of the dyes having structures as described in Formulae 6–19 above can be used to label a nucleoside or nucleotide, a polynucleotide, a polypeptide or other molecule or substrate (e.g., a carbohydrate or a non-biological or biochemical entity) according to methods known to those skilled in the art or described herein.

Determination of Fluorescence Characteristics

The fluorescence characteristics of dyes according to the invention are readily determined according to standard methods known in the art. For example, the excitation spectrum of a dye is determined by monitoring emission at a constant wavelength while the excitation wavelength is varied, generating a curve resembling an absorption spectrum. The emission spectrum of a dye is determined by exciting the dye at a constant wavelength and analyzing the spectrum emitted (either directly, or by analyzing the degree of transmission by a series of filters). The true spectra are determined by normalizing for the wavelength-dependent intensity of the light source and the wavelength-dependent variation of the detector response. Such normalization is usually performed by comparison with the corrected spectra of a known standard (e.g., quinine in sulfuric acid).

Quantum yield and the absolute energy distribution of a fluorescence spectrum are difficult to determine absolutely. In general practice, the quantum yield is usually determined by comparing the fluorescence emission of an unknown with a standard having a known quantum yield to yield a relative quantum yield. Relative quantum yield can be determined by comparing the area under the emission peaks of the known and unknown fluorophores under identical excitation conditions.

The molar extinction coefficient is a direct measure of a dye's ability to absorb light, and is thus an important factor in determining the amount of light a fluorophore can generate. The molar extinction coefficient for a fluorescent dye of the invention is determined using an absorption spectrophotometer.

How to Use the Fluorescent Cyanine Dyes of the Invention

The fluorescent cyanine dyes of the invention may be used in any application, biological or non-biological, for which fluorescent dyes are normally used. For many uses, it will be necessary to first attach the fluorescent cyanine dye to a molecule of interest, for example, a biomolecule. This may be achieved in a number of ways, depending primarily upon the nature of the molecule of interest. Subsequent to the attachment of the dye to a biomolecule, there are a number of applications in which fluorescent cyanine dyes according to the invention are useful in a wide range of applications. Among the methods that benefit most from the novel dyes of the invention are those calling for more than one spectrally distinct fluorescent marker. These include, for example, nucleic acid sequencing reactions, both traditional (Sanger or Maxam-Gilbert) and non-traditional (e.g., sequencing by hybridization), microarray expression screening methods, multiparameter flow cytometry, sub-cellular localization (or co-localization) studies and molecular interaction studies based on fluorescence resonance energy transfer or fluorescence quenching.

Attachment of Fluorescent Cyanine Dyes to a Molecule of Interest

There are at least three primary ways a fluorescent cyanine dye may be covalently attached to a molecule of interest. First, a dye bearing a reactive group can be reacted with a molecule of interest bearing a complementary functional group. Second, a dye bearing a functional group may be reacted with a molecule of interest bearing a reactive group. Finally, a dye with a reactive group may be reacted with a coupling agent and a molecule of interest bearing a functional group for that coupling agent.

Table 1 lists a number of reactive groups and their corresponding complementary functional groups which are routinely used to react with the functional groups common in biomolecules (typically amines, thiols, carboxylic acids, alcohols, phenols, aldehydes and ketones). Other functional groups, such as aryl azides, react indiscriminantly with nearby residues following ultraviolet photolysis. Dyes having common reactive groups (V) that are amino, hydroxy- or thiol-reactive or are photoaffinity labels are typically prepared from preformed dyes containing appropriate precursor substituents, using methods well-known in the art.

complementary group. As a non-limiting example, one of the most commonly used coupling methods for fluorescent dyes involves reaction of a succinimidyl ester on the dye with an amino group on the molecule of interest. Succinimidyl ester-dyes are prepared, for example, by reaction of N-hydroxysuccinimide with a carboxyl group on the dye. A fluorescent dye of the invention bearing a carboxyl group on

TABLE 1

Selected Reactive Substituents and Functional Groups Reactive Therewith

[Chemical structure diagram showing a symmetric molecule with $HO_3S$ and $SO_3H$ groups on terminal indole rings bearing $R_1$ and $R_4$ substituents on nitrogens, connected via conjugated chains to a central bis-indole system with $R_2$ and $R_3$ on the cationic nitrogens]

| Reactive Groups (V) | Corresponding Functional Groups |
|---|---|
| succinimidyl esters | amines |
| anhydrides | amines, alcohols |
| acyl azides | amines |
| isothiocyanates | amines, thiols, alcohols, phenols |
| sulfonyl chlorides, sulfonyl fluorides | amines, phenols, alcohols |
| substituted hydrazines, substituted hydroxylamines | aldehydes, ketones |
| acid halides | amino groups |
| haloacetamides, maleimides | thiols, imidazoles, phenols, amines |
| carobdiimides | carboxyl groups |
| phosphoramidite | alcohol groups |

Examples of approaches to the generation of dye molecules bearing reactive groups include:

a) Succinimidyl esters are typically prepared from dyes having a carboxylic acid substituent using N-hydroxysuccinimide and dicyclohexylcarbodiimide (see below);

b) Acid chlorides are typically prepared from dyes containing carboxylic acid substituents using oxalyl chlorides or thionyl chloride;

c) Isocyanates are typically prepared from dyes containing amine groups using phosgene;

d) Isothiocyanates are typically prepared from dyes having amino substituents using thiophosgene;

e) Reactive haloalkyl groups are typically prepared from dyes having amino groups and an amino-reactive haloacyl or halomethylbenzoyl compound;

f) Photoaffinity labels are typically incorporated by reaction of an amine-containing dye and a known photoaffinity label that also contains an amine-reactive group; and g) Maleimido groups are typically prepared from an amine-containing dye and maleic anhydride.

Alternate synthetic routes to the above reactive functional groups utilize other reagents that are known in the art, and the above methods of preparation are not intended to limit the preparation of the dyes of the current invention to these methods or these reactive groups.

One skilled in the art can readily react a dye containing a given functional group with a molecule of interest with a an alkyl substituent of one of the heterocyclic nitrogens (on either a terminal or a central heterocucle), dissolved in dimethyl formamide (DMF), is reacted with N-hydroxysuccinimide in the presence of dicyclohexylcarbodiimide, resulting in the formation of the succinimidyl ester of the dye. The succinimidyl ester-modified dye is then reacted with an amino group on the molecule of interest, e.g., a polypeptide or a modified nucleic acid, resulting in covalent coupling of the dye to the molecule of interest. Alternatively, the molecule of interest itself may contain or be modified to contain a reactive group such as the NHS group and the dye may contain the amino group.

Those skilled in the art can attach the dyes according to the invention to any molecule or substrate having appropriate functional groups for reaction with dyes bearing complementary reactive groups. However, while not intending to be limited in any way to such applications, the fluorescent dyes according to the invention can be used to particular advantage in biological and biochemical systems. The dyes may be used to label any biomolecule either naturally comprising or modified to comprise a functional group complementary to a reactive group on the dye. Biomolecules of particular interest include nucleotides (ribonucleotides and deoxynucleotides, both naturally occurring forms and synthetic analogs thereof) polynucleotides (single- and double-stranded RNA, DNA, PNAs and combinations thereof), and polypeptides.

1. Labeling of Polynucleotides

In addition to the general chemical methods of attachment of dyes to molecules of interest, there are several methods that are particularly well suited for the attachment of fluorescent dyes of the invention to nucleotides and thereby to DNA. One such method uses aminoallyl-modified (also referred to allylamine-modified) nucleotides. Such nucleotides are well known and are commercially available (e.g., aminoallyl-dUTP is Sigma-Aldrich Catalog No. A-0410). Aminoallyl-modified nucleotides bear an amino group attached to the nucleobase that can be reacted with an NHS-bearing reagent to attach the dye to the nucleotide (see, for example, U.S. Pat. Nos. 5,476,928, and 5,958,691, which are incorporated herein in their entirety by reference). The resulting fluorescently labeled nucleotide (e.g., dATP, dCTP, TTP, dGTP, dUTP, ATP, GTP, CTP, UTP, or analogs of these, such as deoxyinosine, cordycepin, etc.) may be used directly for incorporation studies. Where the fluorescently labeled nucleotide is not readily incorporated by enzymes, it may be necessary to first incorporate a nucleotide modified with an allylamine group and then post-label the probe with the reactive fluorescent dye molecule to generate the labeled probe (see below).

While any nucleotide may bear an aminoallyl modification, perhaps the best suited nucleotide is UTP or dUTP. dUTP is modified by placing the aminoallyl group on the C5 position of the nucleobase. This site does not participate in hydrogen bonding necessary for nucleic acid heteroduplex formation. In contrast, dATP and dCTP nucleotides are generally modified at the C6 position and the C4 position of the nucleobases, respectively. These nucleotides do participate in hydrogen bonding in the heteroduplex, so allylamine modified dATP and dCTP, while useful for fluorescent labeling, are less favored than allylamine-modified dUTP for nucleic acid labeling.

There are two general schemes employed for labeling nucleic acids after the incorporation of allylamine-modified nucleotides. In the first, the allylamine-modified nucleotide is reacted with the NHS ester of biotin, resulting in a biotin-labeled nucleotide which is then incorporated into a probe molecule using an appropriate polymerase enzyme. Generally, the relatively small biotin molecule does not hinder the activity of polymerase enzymes. In order to fluorescently label the probe, the covalently attached biotin is reacted with a fluorescently labeled avidin polypeptide. The avidin may be labeled using any method suited for the attachment of the dye to a polypeptide, including the NHS ester method described herein.

Another means of labeling via allylamine-modified nucleotides dispenses with the biotin/avidin interaction. In this scheme, allylamine-modified nucleotides, without a biotin or other affinity moiety, are enzymatically incorporated into the probe. The allylamine-modified probe is then reacted directly with the NHS ester of a fluorescent dye according to the invention. This method results in direct, covalent attachment of the dye to the probe. Because the allylamine group is even smaller than a biotin molecule, it will generally interfere with enzyme efficiency even less than does a biotin substituent.

In addition to allylamine-modified nucleotides, another means of labeling a nucleic acid probe with a fluorescent dye according to the invention is to attach the dye to a metal containing complex that forms covalent adducts with nucleic acids. In particular, cis-platinum complexes containing a fluorescent dye according to the invention can form adducts with adenine and guanine bases in nucleic acids, resulting in fluorescent labeling of those nucleic acids. Methods for such labeling are described in U.S. Pat. Nos. 5,714,327 and 5,985,566, which are incorporated herein in their entirety by reference.

Following labeling of a nucleic acid by any of the above-described methods or by another method known in the art, the labeled nucleic acid is used for hybridization studies in a manner essentially the same as any other fluorescently labeled nucleic acid probe. Hybridization methods for fluorescently labeled nucleic acid probes are well known in the art.

2. Labeling of Polypeptides

Polypeptides may be labeled with fluorescent molecules bearing reactive groups, such as those listed in Table 1, that react with side groups on the polypeptide. As with polynucleotide labeling, while they are not the only reagents useful for this purpose, NHS esters of fluorescent labels are commonly used for covalently attaching fluorophores to polypeptides. The NHS ester labeling group will covalently attach to any primary amino group on the peptide or polypeptide to be labeled (e.g., lysine and arginine residues). When the pH is above 7.0, the NHS ester labeling group is subject to nucleophilic attack by the amine group on the peptide or polypeptide. As a result, the NHS group is displaced from the fluorescent dye ester to form a stable amide bond between the fluorescent dye and the polypeptide or peptide.

As a non-limiting example, an antibody can be labeled with an NHS ester of a fluorescent dye of the invention as follows. The antibody is dissolved in phosphate buffered saline (PBS) at pH 7.4. The pH is then adjusted to pH 9.4 using 0.1 M sodium carbonate. Fluorescent cyanine dye NHS ester is added, followed by 30 minute incubation at room temperature. Dye may be added in various molar ratios relative to the antibody, but generally a ratio greater than 5 is preferred. Higher ratios generally correlate with a larger number of fluorescent molecules per polypeptide. However, depending upon the polypeptide and the purpose for which it is being labeled, it may not be desirable to saturate all possible label attachment sites. The labeling ratio is readily adjusted by one skilled in the art to suit a particular need. Following incubation, unreacted label may be removed by any appropriate means, including, for example, gel filtration chromatography.

Detection of Fluorescent Labels

Molecules labeled with fluorescent dyes according to the invention may be detected in a variety of ways. The detecting method can utilize a light source that irradiates a mixture containing the labeled species with light having specific wavelengths. Upon excitation by the light source, fluorescent emission by the label is detected by a device sensitive to the wavelengths emitted. Detection devices include, for example, fluorescence spectrometers, absorption spectrophotometers, fluorescence microscopes, transmission light microscopes, flow cytometers, fiber optic sensors and immunoassay instruments. Because the fluorescent dyes of the invention are well suited for use in array and microarray analyses, detection devices adapted to or specific for these formats are particularly useful. Plate readers capable of scanning for fluorescence signal and fluorescence microarray detection arrangements are known in the art.

Methods Employing Fluorescent Dyes According to the Invention

Once attached to a biomolecule or other molecule of interest, the water soluble fluorescent dyes according to the invention may be used in any application for which fluorescent dyes are normally used. Because the dyes according to the invention have a range of excitation and emission spectra, they are well suited for use in systems in which a plurality of distinctly detectable dyes are required. Dyes according to the invention may be paired with other dyes according to the invention, or they may be paired or grouped with other known dyes having appropriate spectral characteristics.

In many circumstances, it will be advantageous to select a plurality of dyes which are excited by a similar spectrum of light but that emit at distinguishable wavelengths. This format simplifies the process of detection in that only one excitation energy is necessary for differential target detection, rather than having to scan through different excitation spectra for each distinct label. This format is particularly useful in dynamic processes such as multiparameter flow cytometry, where it may avoid the need for multiple excitation energy filters or sources and can make the process more efficient. It is also an advantageous arrangement when performing high throughput analyses using more than one distinct label.

In addition to methods utilizing a plurality of distinctly detectable labels, water soluble fluorescent cyanine dyes according to the invention can be paired with other fluorescent dyes for use in fluorescence resonance energy transfer or fluorescence quenching assays to monitor molecular interactions. Fluorescence energy transfer is reviewed in Matyus, 1992, *J. Photochem. Photobiol. B*. 12: 323–337; Lakowicz, 1983, *Principles of Fluorescence Spectroscopy*, Plenum Press, New York; and in Jovin & Jovin, 1989, *Cell Structure and Function by Microspectrofluorometry*, eds. E. Kohen and J. G. Hirschberg, Academic Press, each of which is incorporated herein by reference. A first fluorescent dye whose emission spectrum overlaps the excitation spectrum of a second dye or fluorophore can undergo non-radiative energy transfer to the second dye, resulting in emission at the wavelength characteristic of the second dye when a mixture of the two is irradiated with light that excites the first, but not the second fluorescent dye. The non-radiative transfer will occur only when the two fluorophores are in close proximity, making the phenomenon useful for the detection of molecular interactions (e.g., protein:protein, protein:nucleic acid, nucleic acid:nucleic acid interactions or the interaction of drugs or chemicals with protein, nucleic acid or other target molecules), and for evaluation of compounds or conditions that alter those interactions. Assays of this kind are well known in the art.

The measurement of molecular interactions enabled by energy transfer can also permit the detection and quantitation of the amount of an analyte. When the presence of an analyte either induces or disrupts the association of a donor/acceptor pair, the resulting change in fluorescent emission serves to indicate the presence and/or amount of the analyte. This principle has been extensively exploited in the area of nucleic acid detection and quantitation in the form of "molecular beacons", which bear either a donor/acceptor or a fluorophore/quencher pair situated such that fluorescent emission is changed when the beacon probe hybridizes to a target nucleic acid. The change may be, for example, relief of quenching caused by disruption of probe secondary structure resulting in separation of fluorophore and quencher. Alternatively, the change may be a shift in fluorescence emission from the acceptor's wavelength to the donor's wavelength. There are numerous variations on the beacons theme. U.S. Pat. Nos. 5,210,015, 5,691,146, 5,891, 639, 5, 914,230, 5,945,283, 6,030,787 and 6,090,552, incorporated herein by reference, teach but a few of these useful variations.

EXAMPLES

Example 1

Synthetic Scheme for the Synthesis of Dyes Containing a Linear Fused Heterocycle The steps for the synthesis of dyes containing a linear fused heterocycle are illustrated in FIG. 1. Bold numerals in the following text refer to numbered products and intermediates in the figure. The specific example is for the synthesis of a dye according to Formula 7 herein, but the general synthetic scheme may be varied by one of skill in the art to achieve other dyes with a linear fused heterocycle as described herein (e.g., dyes according to Formulae 6, 8–13 and 19).

A. Synthesis of 2,6-Dimethyl-benzo[1.2.5.4]bis-thiazol (I in FIG. 1)

A mixture of 1,3-dichloro-4,6-dinitrobenzene (15 g) in EtOH (250 mL) was brought to reflux temperature. A mixture of $Na_2 9H_2O$ (15 g) and sulfur (2 g) was ground with a mortar and pestle and added as a powder in small portions over the course of an hour to the refluxing mixture. The reaction is highly exothermic. After addition was accomplished the mixture was left at reflux temperature a further two hours. The mixture was cooled to room temperature and filtered. The resultant yellow powder was washed several times with boiling aqueous ethanol (3 ×100 mL). A portion of the above yellow powder (10 g) was mixed with acetic acid (80 mL), and tin (II) chloride dihydrate (70 g) was added in portions. The mixture was brought to reflux temperature in stages, with much exothermic activity observed at 60° C. After refluxing for 2 h, the mixture was cooled to room temperature and acetic anhydride (70 mL) was added. The mixture was heated at reflux temperature for 36 h. The mixture was cooled to room temperature and neutralized by the addition of sodium carbonate (an excessive amount of $Na_2CO_3$ is required for this neutralization, and addition of extra water was required. Also, addition of base should be fairly conservative or much bubbling occurs). The mixture was filtered, and the filtrate was extracted with hexane (3×100 mL). The solid was then continuously extracted with hexane for 22 h. The combined organic extracts were combined, dried, and filtered. The crude reaction mixture was recrystallized from hexane to afford the product as white crystals (1.2 g; see FIG. 1, compound I).

B. Bisalkyation of 2,6-Dimethyl-benzo[1.2.5.4]bis-thiazol

Bislakylation of the heterocycle required first recrystallizing the 2,6-Dimethyl-benzo[1.2.5.4] bis-thiazol from either hexane or ethanol, and then further purifying by sublimation. Recrystallization afforded high quality crystals (that were homogenous on TLC), and sublimation resulted in a somewhat amorphous white solid. Interestingly, the melting point of the sublimed material was 150° C., significantly higher than that of the solely recrystallized material (144° C.).

For the bisalkylation, 2,6-dimethyl-benzo[1.2.5.4]bisthiazol (I in FIG. 1; 175 mg) was melted in a test-tube in an oil-bath at 165° C. Dimethylsulfate (0.9 mL) was added in one portion, and the mixture was stirred for 5 min. Water (1.3 mL) was added, and the mixture was removed from the heat. After cooling, an aqueous sodium perchlorate solution was added, fomenting a grayish precipitate which was collected by filtration. MS analysis was performed on the dimethylated product (III in FIG. 1): MS expected for the dimethylated product (III) expected $C_{12}H_{14}S_2N_2$: 250.2; Found: 250.3 (m+e$^-$). A small amount of monoalkylated product (II) was also obtained in low yield.

A mixture of 1-(carboxypentyl)-2,3,3-trimethylindolium bromide (2 g, 5.6 mmole), N,N-diphenylformamidine (1.25 g, 6.4 mmole) in acetic acid (8 mL) was heated at 110° C. for 4 h. The solvent was removed under reduced pressure. Purification of the intermediate, 2-(2-anilinovinyl)-1-(carboxypentyl)-,3,3-dimethylindolium bromide (IV) was achieved by column chromatography eluting initially with pure CHCl$_3$ and gradually adding methanol until methanol comprised 10% by volume of the eluent. MS Expected for $C_{24}H_{29}N_2O_2$: 377.2; Found 377.6.

C. Synthesis of Dye

To a solution of III (52 mg, 0.166 mmol) in 1:1 (v/v) pyr-Ac$_2$O (1 mL) was added indolenine IV (93 mg, 0.250 mmol) and the mixture was heated at 110° C. overnight. The solution was added to an excess of hexane. The hexane was removed. A portion of the resultant blue sludge was dissolved in MeOH and applied to a prep-TLC plate. Elution was accomplished with 6:1 (v/v) CHCl$_3$:MeOH. Only one blue band was evident, and this was isolated. Purification of dyes 1a and 1b was accomplished by preparative thin layer chromatorgraphy (Analtech). 1a: MS Expected for $C_{29}H_{32}N_3O_2S_2$ 518.19 Found: 518.7 (m+e$^-$). The dyes were evaluated on a Shimadzu RF-1505 spectrofluorophotometer. Fluorescence $\lambda_{max}$ ex: 558 nm, $\lambda_{max}$ em: 574 nm; 1b: MS Expected for $C_{48}H_{56}N_4O_4S_2$: 816.2. Found: 408.5 (z=2), 815.7(m+e$^-$). $\lambda_{max}$ ex: 557 nm, $\lambda_{max}$ em: 572 nm;

Dimethyl linear expected 533.2 found m/e532.8 ex 558 nm em 571 nm

Example 2

Figure 2:
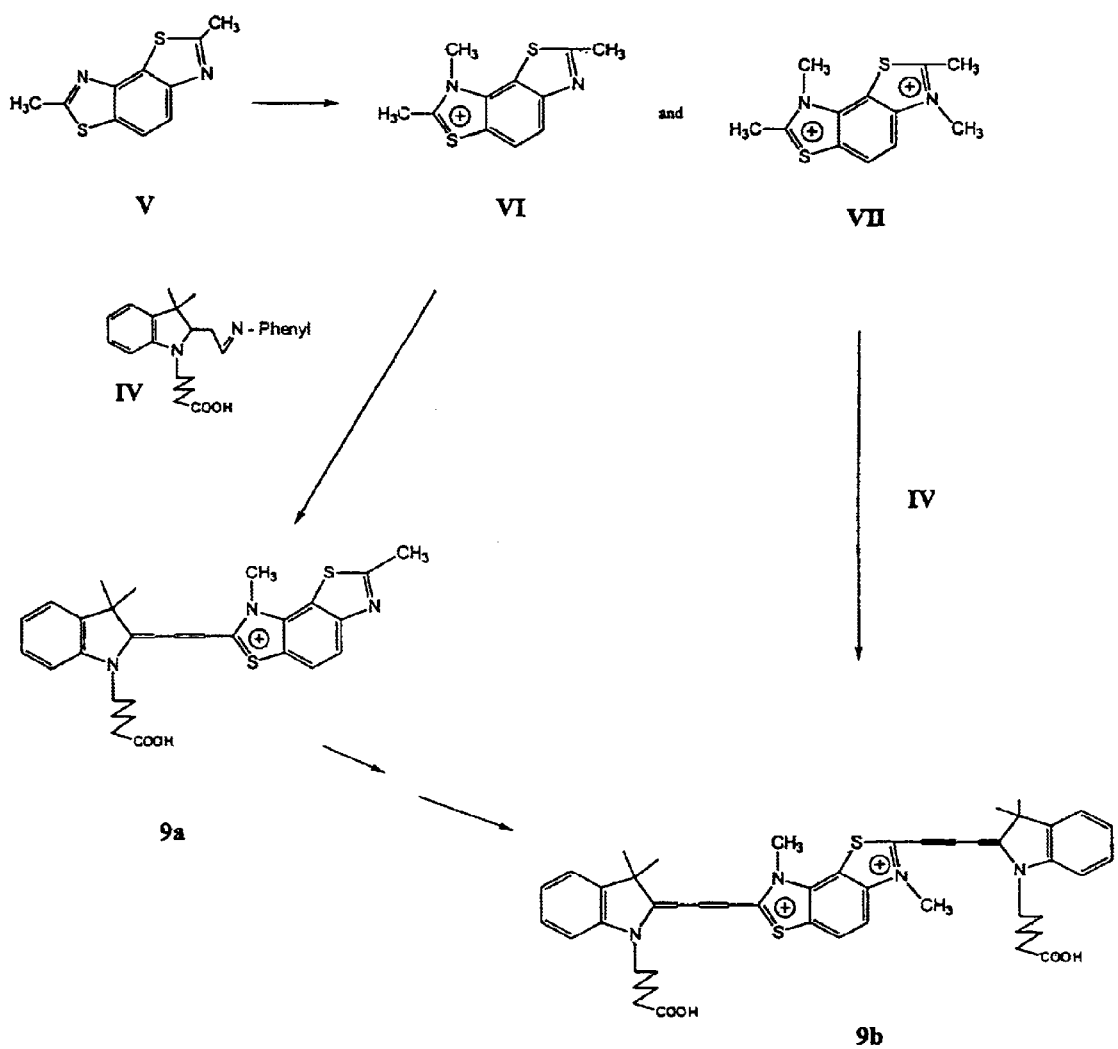
FIG. 2 shows a schematic diagram of steps involved in the synthesis of a dye comprising a bent-cored fused hetero cycle.

Synthetic Scheme for the Synthesis of Dyes Containing an Angular Fused Heterocycle A synthetic scheme for the synthesis of dyes according to the invention that have an angular heterocyclic core is shown in FIG. 2. Bold numerals in the text refer to numbered products and intermediates in the figure.

A. Synthesis of 3,8-dimethylbenzo[1,2-d:3,4-d']bisthiazole, bis triflate salt (VI).

To a solution of 2.86 g of Benzo[1,2-d:3,4-d']bisthiazole (V), prepared as described by Edge [J. Chem. Soc. 19 ] in 50 ml of dry acetonitrile was added 4.4 ml of methyltriflate. The solution was allowed to stir at room temperature for two hours, after which the resulting white precipitate was filtered. :MS Expected for $C_{29}H_{32}N_3O_2S_2$ 518.19 Found 518.7 (m+e$^-$). After an additional 4 hours a second crop of precipitate was filtered. This contained a mixture of dimethyl (VI) and monomethyl (VII) products.

B. Synthesis of Dyes 9a, 9b

To a solution of VI (52 mg, 0.166 mmol) in 1:1 (v/v) pyr-Ac$_2$O (1 mL) was added indolenine IV (93 mg, 0.250 mmol) and the mixture was heated for 4 hours at 110° C. The solution was added to an excess of ethyl ether, decanted and the insoluble residue taken up in 50 ml of methanol. Purification of dyes 9a and 9b was accomplished by preparative thin layer chromatorgraphy (Analtech). Elution was accomplished with 6:1 (v/v) CHCl$_3$:MeOH. 9a: MS Expected for $C_{29}H_{32}N_3O_2S_2$, 518.19. Found: 518.7 (m+e$^-$). Fluorescence $\lambda_{max}$ ex: 558 nm, $\lambda_{max}$ em: 574 nm. 9b: MS Expected for $C_{48}H_{56}N_4O_4S_2$, 816.2. Found: 408.5 (z=2), 815.7 (m+e$^-$). $\lambda_{max}$ ex: 557 nm, $\lambda_{max}$ em: 572 nm;

The general scheme shown above can be varied by one of skill in the art to generate dyes according to Formulae 14–17.

Example 3

Labeling Oligonucleotide Probe with Fluorescent Dye of the Invention

Dyes according to the invention are attached to biomolecules, such as nucleotides, nucleosides, oligonucleotides, amino acids or polypeptides according to standard chemical methods via complementary reactive groups on the dye and the biomolecule, respectively. As a non-limiting example, the following describes the labeling of an oligonucleotide with a dye of the invention.

Dye according to the invention (1 mg) is dissolved in 200 μl of DMSO and immediately added to a solution of amino oligonucleotide 5'-X AAA CCC GGG AGC TCG AAT TCC CTA TAG GTA GTC GTA TTA AAT TCG TAG TCA TGT CAT AAC TGT TTC CTG TGT G-3' (1 mg, X=5' amino C-12) (SEQ ID NO: 1) in 500 μl of 0.1 M sodium bicarbonate solution (pH 8.5). The solution is vortexed briefly and placed on a turntable for 18 hours at room temperature. Excess free dye is removed using a NAP-10 column and the resulting solution is purified by HPLC.

What is claimed is:

1. A fluorescent cyanine dye having the formula:

$$T_1(-CH=)_{n_1}A(-CH=)_{n_2}T_2$$

wherein:

$n \geq 1$ and $n_1$ is the same as or different from $n_2$;

A comprises the formula:

wherein:

$X_1$ and $Y_1$ are selected from the group consisting of $C(CH_3)_2$, $CH=CH$, O, N, S, Se and Te and either $X_1$ or $Y_1$ is N;

$X_2$ and $Y_2$ are selected from the group consisting of $C(CH_3)_2$, $CH=CH$, O, N, S, Se and Te and either $X_2$ or $Y_2$ is N; or A comprises the formula:

wherein:

$Z_1$ and $Y_1$ are selected from the group consisting of $C(CH_3)_2$, $CH=CH$, O, N, S, Se and Te and either $Z_1$ or $Y_1$ is N;

$Z_2$ and $Y_2$ are selected from the group consisting of $C(CH_3)_2$, $CH=CH$, O, N, S, Se and Te and either $Z_2$ or $Y_2$ is N; and wherein a and b are 0 or 1, and a+b=1; and where X, Y or Z is N, $R_2$ and $R_3$ are substituents on N and are the same or different and are selected from the group consisting of H, methyl, ethyl, $C(CH_3)_2$ and $(CH_2)_qV$, wherein q is an integer from 1 to 25 and V is a reactive group or H; and wherein:

T1 and T2 are the same or different and have the formula:

wherein:

Q is selected from the group consisting of O, S, $CH_2$, $(CH=CH)$ and $C(CH_3)_2$;

$R_1$ and $R_4$ are the same or different and are selected from the group consisting of H, methyl, ethyl and $(CH_2)_qV$, wherein q is an integer from 1 to 25 and V is a reactive group or H;

each of $W_{1-8}$ is the same or different and may be H or a hydrophilic moiety;

at least one occurrence of W is a hydrophilic moiety; and wherein at least one of $R_1$–$R_4$ has a reactive group.

2. The fluorescent cyanine dye of claim 1 wherein one or both of $Y_1$ and $Y_2$ are N.

3. The fluorescent cyanine dye of claim 2 wherein one or both of $X_1$ and $X_2$ are S.

4. The fluorescent cyanine dye of claim 2 wherein one or both of $X_1$ and $X_2$ are O.

5. The fluorescent cyanine dye of claim 2 wherein one or both of $X_1$ and $X_2$ are $CH_2$.

6. The fluorescent cyanine dye of claim 2 wherein one or both of $X_1$ and $X_2$ are $(CH=CH)$.

7. The fluorescent cyanine dye of claim 2 wherein one or both of $Y_1$ and $Y_2$ are S.

8. The fluorescent cyanine dye of claim 1 wherein $Z_1$ and $Y_2$ are S.

9. The fluorescent cyanine dye of claim 1 wherein $Y_1$ and $Z_2$ are S.

10. The fluorescent cyanine dye of claim 1 wherein Q is $CH_2$.

11. The fluorescent cyanine dye of claim 1 wherein Q is $C(CH_3)_2$.

12. A composition comprising a fluorescent cyanine dye of claim 1.

13. A fluorescent cyanine dye having the formula:

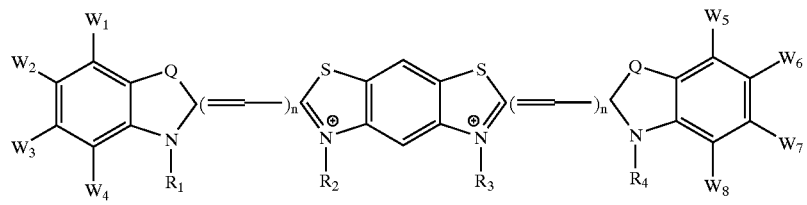

wherein:

$n \geq 1$;

Q is selected from the group consisting of O, S, $CH_2$, (CH=CH) and $C(CH_3)_2$;

$R_1$–$R_4$ are the same or different and are selected from the group consisting of H, methyl, ethyl and $(CH_2)_qV$, wherein q is an integer from 1 to 25 and V is a reactive group or H, and at least one of R1–R4 has a reactive group;

each of $W_{1-8}$ is the same or different and may be H or a hydrophilic moiety; and at least one occurrence of W is a hydrophilic moiety.

14. A composition comprising the dye of claim 13.

15. A fluorescent cyanine dye having the formula:

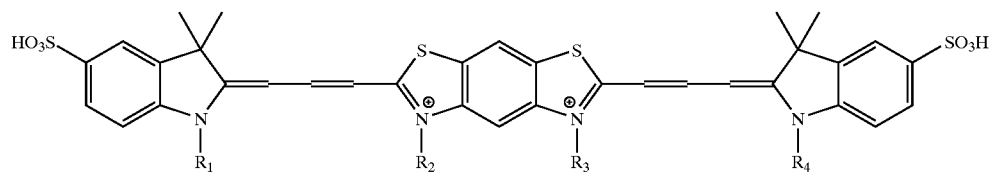

wherein $R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group.

16. A fluorescent cyanine dye having the formula:

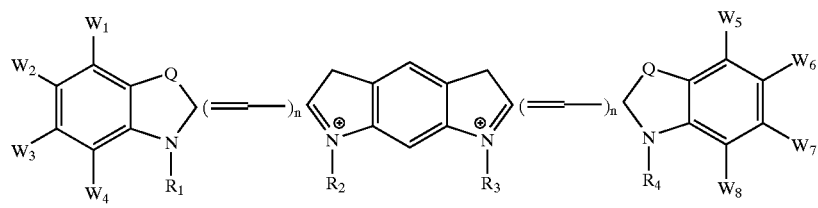

wherein:

n≧1;

Q is selected from the group consisting of O, S, $CH_2$, (CH=CH) and $C(CH_3)_2$;

R1–R4 are the same or different and are selected from the group consisting of H, methyl, ethyl and $(CH_2)_qV$, wherein q is an integer from 1 to 25 and V is a reactive group or H, and at least one of R1–R4 has a reactive group;

each of $W_{1-8}$ is the same or different and may be H or a hydrophilic moiety; and at least one occurrence of W is a hydrophilic moiety.

17. A composition comprising the dye of claim 16.

18. A fluorescent cyanine dye having the formula:

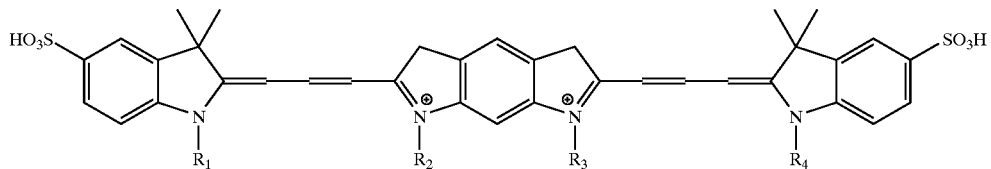

wherein $R_1-R_4$ are the same or different and are selected from the group consisting of H, methyl, ethyl and $(CH_2)_qV$, wherein q is an integer from 1 to 25 and V is a reactive group or H, and at least one of $R_1-R_4$ has a reactive group.

19. A fluorescent cyanine dye having the formula:

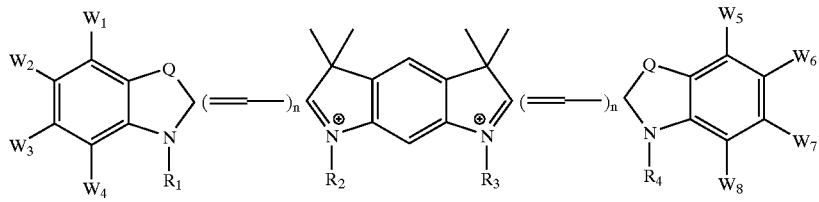

wherein:

n≧1;

Q is selected from the group consisting of O, S, $CH_2$, (CH=CH) and $C(CH_3)_2$;

R1–R4 are the same or different and are selected from the group consisting of H, methyl, ethyl and $(CH_2)_qV$, wherein q is an integer from 1 to 25 and V is a reactive group or H, and at least one of R1–R4 has a reactive group;

each of $W_{1-8}$ is the same or different and may be H or a hydrophilic moiety; and at least one occurrence of W is a hydrophilic moiety.

20. A composition comprising the dye of claim 19.

21. A fluorescent cyanine dye having the formula:

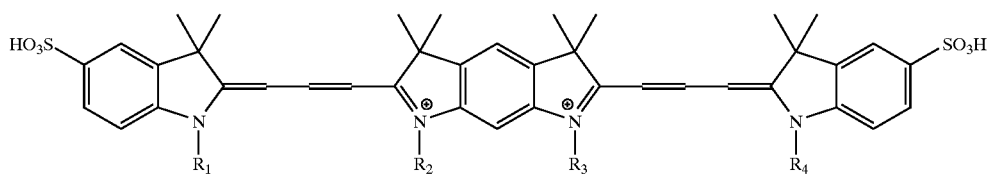

wherein $R_1$–$R_4$ are the same or different and are selected from the group consisting of H, methyl, ethyl and $(CH_2)_q V$, wherein q is an integer from 1 to 25 and V is a reactive group or H, and at least one of $R_1$–$R_4$ has a reactive group.

22. A fluorescent cyanine dye having the formula:

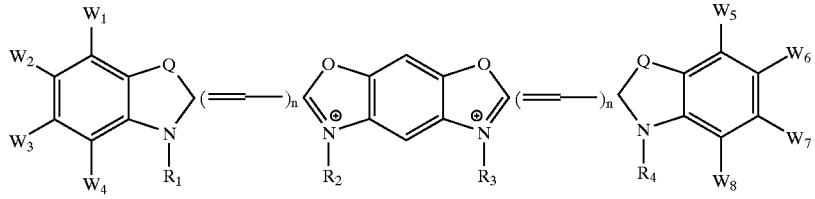

wherein:

$n \geq 1$;

Q is selected from the group consisting of O, S, $CH_2$, (CH=CH) and $C(CH_3)_2$;

$R_1$–$R_4$ are the same or different and are selected from the group consisting of H, methyl, ethyl and $(CH_2)_q V$, wherein q is an integer from 1 to 25 and V is a reactive group or H, and at least one of $R_1$–$R_4$ has a reactive group;

each of $W_{1-8}$ is the same or different and may be H or a hydrophilic moiety; and at least one occurrence of W is a hydrophilic moiety.

23. A composition comprising the dye of claim 22.

24. A fluorescent cyanine dye having the formula:

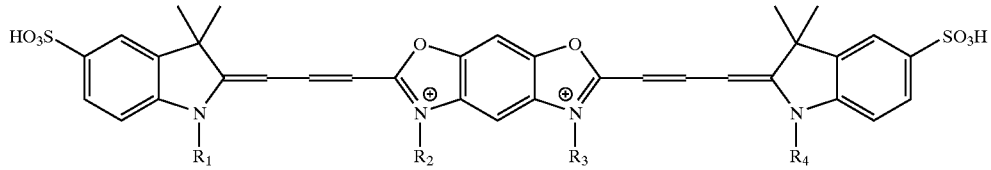

wherein $R_1$–$R_4$ are the same or different and are selected from the group consisting of H, methyl, ethyl and $(CH_2)_q V$, wherein q is an integer from 1 to 25 and V is a reactive group or H, and at least one of $R_1$–$R_4$ has a reactive group.

25. A fluorescent cyanine dye having the formula:

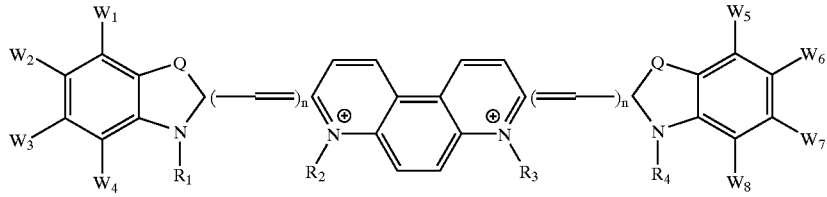

wherein q is an integer from 1 to 25 and V is a reactive group or H, and at least one of $R_1$–$R_4$ has a reactive group;

each of $W_{1-8}$ is the same or different and may be H or a hydrophilic moiety; and at least one occurrence of W is a hydrophilic moiety.

26. A composition comprising the dye of claim 25.

27. A fluorescent cyanine dye having the formula:

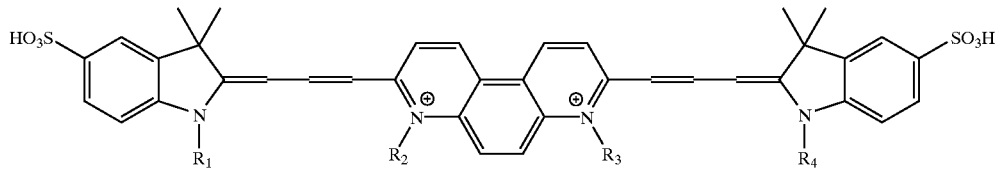

wherein $R_1$–$R_4$ are the same or different and are selected from the group consisting of H, methyl, ethyl, $C(CH_3)_2$ and $(CH_2)_qV$, wherein q is an integer from 1 to 25 and V is a reactive group or H, and at least one of $R_1$–$R_4$ has a reactive group.

28. A fluorescent cyanine dye having the formula:

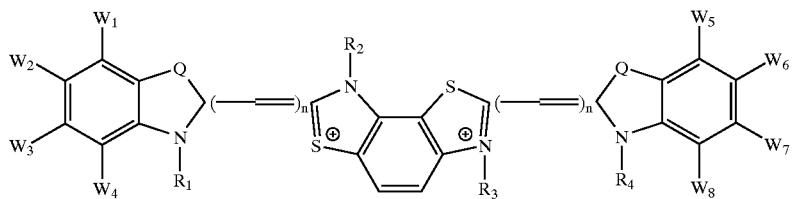

wherein:

$n \geq 1$;

Q is selected from the group consisting of O, S, $CH_2$, (CH=CH) and $C(CH_3)_2$;

$R_1$–$R_4$ are the same or different and are selected from the group consisting of H, methyl, ethyl and $(CH_2)_qV$, wherein q is an integer from 1 to 25 and V is a reactive group or H, and at least one of $R_1$–$R_4$ has a reactive group;

each of $W_{1-8}$ is the same or different and may be H or a hydrophilic moiety; and at least one occurrence of W is a hydrophilic moiety.

29. A composition comprising the dye of claim 28.

30. A fluorescent cyanine dye having the formula:

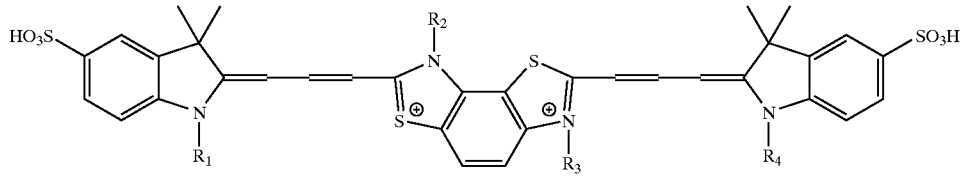

wherein R₁–R₄ are the same or different and are selected from the group consisting of H, methyl, ethyl and $(CH_2)_qV$, where in q is an integer from 1 to 25 and V is a reactive group or H, and at least one of R₁–R₄ has a reactive group.

31. A fluorescent cyanine dye having the formula:

wherein:

$n \geq 1$;

Q is selected from the group consisting of O, S, $CH_2$, (CH=CH) and $C(CH_3)_2$;

R₁–R₄ are the same or different and are selected from the group consisting of H, methyl, ethyl and $(CH_2)_qV$, wherein q is an integer from 1 to 25 and V is a reactive group or H, and at least one of R₁–R₄ has a reactive group;

each of $W_{1-8}$ is the same or different and may be H or a hydrophilic moiety; and at least one occurrence of W is a hydrophilic moiety.

32. A composition comprising the dye of claim 30.

33. A fluorescent cyanine dye having the formula:

wherein R₁–R₄ are the same or different and are selected from the group consisting of H, methyl, ethyl and $(CH_2)_qV$, wherein q is an integer from 1 to 25 and V is a reactive group or H, and at least one of R₁–R₄ has a reactive group.

34. A fluorescent cyanine dye of any one of claims 1, 13, 16, 19, 22, 25 or 28 that comprises a succinimide ester linked to a heterocyclic nitrogen.

35. A nucleoside or nucleotide labeled with a flourescent cyanine dye of any one of claims 1, 13, 16, 19, 22, 25 or 28.

36. A polynucleotide labeled with a flourescent cyanine dye of any one of claims 1, 13, 16, 19, 22, 25 or 28.

37. A polypeptide labeled with a flourescent cyanine dye of any one of claims 1, 13, 16, 19, 22, 25 or 28.

38. A method of labeling a nucleotide or nucleoside, said method comprising contacting a fluorescent cyanine dye of claim 1 with said nucleotide or nucleoside.

39. A method of labeling a nucleic acid, said method comprising contacting a fluorescent cyanine dye of claim 1 with said nucleic acid.

40. The method of claim 39 wherein said nucleic acid comprises an allyl-amine-modified nucleotide, and said dye comprises an NHS group.

41. A method of labeling a polypeptide, said method comprising contacting a fluorescent cyanine dye of claim 1 with said polypeptide.

42. A method of labeling a nucleic acid, said method comprising contacting said nucleic acid with a cis-platinum complex comprising a fluorescent cyanine dye of claim 1.

43. A method of determining a nucleic acid sequence, said method comprising performing a nucleic acid sequencing reaction in the presence of a labeled nucleotide of claim 35.

44. The method of claim 43, wherein said contacting is performed in the presence of a second nucleotide comprising a fluorescent dye that is spectrally distinct from the dye on said first nucleotide.

45. A method of determining a nucleic acid sequence, said method comprising determining a nucleic acid sequence on a nucleic acid comprising a fluorescent cyanine dye of claim 1.

46. A method of detecting a polynucleotide, said method comprising detecting a polynucleotide comprising a labeled nucleotide of claim 35.

47. A method of detecting a polynucleotide, said method comprising detecting a polynucleotide comprising a fluorescent cyanine dye of claim 1.

48. The method of claim 47, wherein said detecting is performed on a nucleic acid microarray.

49. A method of detecting a polypeptide, said method comprising detecting a polypeptide comprising a fluorescent cyanine dye of claim 1.

* * * * *